(12) United States Patent
Ernst

(10) Patent No.: US 6,511,829 B1
(45) Date of Patent: Jan. 28, 2003

(54) GFP-ANNEXIN FUSION PROTEINS

(75) Inventor: Joel D. Ernst, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 656 days.

(21) Appl. No.: 08/948,276

(22) Filed: Oct. 9, 1997

(51) Int. Cl.[7] .......................... C12P 21/02; C12N 1/21; C07K 14/435; C07H 21/04
(52) U.S. Cl. .............. 435/69.7; 435/252.3; 435/252.33; 530/350; 536/23.4; 536/23.5
(58) Field of Search .............................. 435/69.7, 252.3, 435/252.33; 530/350; 536/23.4, 23.5

(56) References Cited

U.S. PATENT DOCUMENTS 5,491,084 A * 2/1996 Chalfie et al. .............. 435/189

FOREIGN PATENT DOCUMENTS

JP 08256770 * 10/1996

OTHER PUBLICATIONS

Ernst et al. (1994) Biochem. Biophys. Res. Com., vol. 200, pp. 867–876.*
Okabayashi et al. (Oct. 24, 1996) Gene, vol. 177, pp. 69–76.*
Brownawell et al. (Aug. 29, 1997) J. Biol. Chem., vol. 272, pp. 22182–22190.*
Cubitt et al. (1995) TIBS, vol. 20, pp. 448–455.*

* cited by examiner

Primary Examiner—Elizabeth Slobodyansky
(74) Attorney, Agent, or Firm—Richard Aron Osman

(57) ABSTRACT

Bifunctional green fluorescent protein (GFP)-annexin fusion proteins combine the inherent strong visible fluorescent properties of GFPs with the anionic phospholipid binding specificity of annexins. Recombinant host cells, especially bacteria, are used to efficiently express the fusion proteins in high yield and soluble form, suitable for rapid, one-step affinity purification. Uses include of selective cellular and biochemical labeling, particularly anionic species, such as selectively labeling apoptotic cells.

21 Claims, No Drawings

GFP-ANNEXIN FUSION PROTEINS

The research carried out in the subject application was supported in part by NIH Grant #HL56001 (0577508-92-002). The government may have rights in any patent issuing on this application.

INTRODUCTION

1. Field of the Invention

The field of the invention is fluorescently-labeled proteins which specifically bind certain phospholipids.

2. Background

The annexins are a family of proteins that specifically bind anionic phospholipids, including phosphatidylserine, in a calcium-dependent manner (Blackwood, R. A. and Ernst, J. D. (1990)Biochem. J. 266, 195–200; Seaton, B. A. (1995) Annexins, R. G. Landes, Austin, Tex.; Cell Mol Life Sci, June 1997;53(6), entire issue). While all annexins bind phosphatidylserine and calcium, they vary in their affinity for phosphatidylserine: for example, at saturating concentrations of calcium (i.e., =1.0 mM), annexin V exhibits a 2- to 160-fold higher affinity for phosphatidylserine compared to other members of the annexin family (Tait, J. F., et al. (1988) Biochemistry 27, 6268–6276; Ernst, J. D., Mall, A. and Chew, G. (1994) Biochem Biophys Res Com 200, 867–876). Annexin binding specificities have been exploited for biological targeting (Tait et al., 1995, J. Biol. Chem. 270, 21594–21599; Oshawa et al, 1996, J. Neurochem. 67, 89–97; Okabayashi et al., 1996, Gene 177, 69–76).

Apoptosis, or programmed cell death, is a universal process that is important in development of multicellular organisms, regulation of the immune system, and clearance of abnormal (including neoplastic and virus-infected) cells (Thompson, C. B. (1995) Science 267, 1456–62). Among the early manifestations of apoptosis in all cell types studied to date is loss of the asymmetric distribution of plasma membrane phospholipids, which results in exposure of anionic phospholipids (including phosphatidylserine) on the extracellular leaflet of the plasma membrane. This exposure of phosphatidylserine, and thus apoptosis, can be detected by various methods, including binding of labeled atinexins (Koopman, G., et al. (1994) Blood 84, 1415–20; Martin, S. J., et al. (1995) J Exp Med 182, 1545–56; Broaddus, V. C., et al. (1996) J Clin Invest 98, 2050–2059; Zhang G, et al., 1997, Biotechniques, Sep;23(3):525–531. Recently, annexin binding specificity has been correlated with other cellular pathology, e.g. King K. B. (1997) J Cell Biochem 65(2), 131–144. Most studies to date have used FITC-annexin V and flow cytometry to identify and enumerate apoptotic cells. Labeling annexin V with FITC requires multiple manipulations of the protein and results in a heterogeneous mixture of labeled protein molecules which vary in the number and position of bound FITC molecules. Moreover, the amino acid residue of annexin V that is most readily available for labeling by FITC is on or near the phospholipid-binding surface, which results in quenching of FITC-annexin V fluorescence by 40–50% upon binding phospholipid membranes (Tait, 1988; Ernst, 1994; supra).

In an effort to circumvent these limitations of FITC-annexins, the present inventor sought to prepare annexins that were labeled homogeneously and that did not change fluorescence properties upon binding membrane phospholipids. Described herein are the preparation and characterization of endogenously fluorescent phosphatidylserine-binding proteins containing *Aequorea Victoria* green fluorescent proteins (GFPs) fused to annexins. It is shown that these reagents offer highly sensitive detection of apoptotic cells by flow cytometry or fluorescent microscopy, and offer several advantages to chemically modified annexins.

SUMMARY OF THE INVENTION

The invention provides methods and compositions relating to *Aequorea Victoria* GFP-annexin fusion proteins; particularly, recombinant polypeptides comprising a bifunctional green fluorescent protein—annexin fusion protein providing an equivalent or enhanced measured fluorescent property of the green fluorescent protein and an equivalent or enhanced measured binding specificity of the annexin. In a particular embodiment, the fusion protein comprises a full-length N-terminal GFP fused to a full-length annexin V through a linker comprising an alanine, wherein the fused GFP and annexin moieties provide greater or equal fluorescent intensity and anionic phospholipid binding affinity, respectively, than do the corresponding unfused GFP and annexin proteins.

The invention also provides host cells expressing the subject proteins, including bacteria expressing the subject proteins in soluble form, and methods of using such cells to make the fusion proteins. Uses of the subject fusion proteins include selective cellular and biochemical labeling, particularly anionic species, such as anionic phospholipids. In a particular embodiment, the fusion proteins are used to selectively label apoptotic, dead and/or injured cells.

DESCRIPTION OF PARTICULAR EMBODIMENTS OF THE INVENTION

The subject bifunctional GFP-annexin fusion proteins combine the inherent intense fluorescent properties of green fluorescent proteins with the binding specificity of annexins. The GFPs derive from the jellyfish *Aequorea victoria*; see e.g. U.S. Pat. No. 5,491,084 for definition, and include variants offering a variety of different excitation and emission wavelengths; see e.g. Heim and Tsien, 1996, Current Biology 6, 178–182. The GFP moiety of the fusion proteins provide an equivalent or enhanced measured qualitative and/or quantitative fluorescent property compared with the corresponding unfused GFP protein. Preferred fluorescent properties are emission and/or excitation peaks, preferably an maximum fluorescent emission peak in unchanged or detectably optimized wavelength and/or undiminshed or enhanced in magnitude or total intensity.

The subject annexins may be derived from a variety of eukaryotic sources, see e.g. Cell Mol Life Sci, June 1997;53 (6), entire issue, esp. Liemann S, Huber R, at 516–521 and Morgan R O, at 508–515, and any of the at least thirteen distinct annexin types may be used. The annexin moiety of the fusion proteins provide an equivalent or enhanced measured qualitative and/or quantitative binding specificity compared with the corresponding unfused annexin protein. Preferred binding specificities have equivalent or enhanced affinity for particular anionic cellular components, particularly phospholipids, such as phosphotidylserine.

The GFP and annexin moieties may be separated by a linker peptide, typically from about 1 to 50 residues, which facilitates or at least does not interfere with the requisite bifunctionality of the fusion proteins. The linker may enhance the conformational opportunities of the GTP and annexin moieties and/or provide a third functionality to the fusion protein, e.g. epitopes, post-translational processing sites, etc. Exemplary linkers include alanine or polyalanine, glycine or polyglycine, epitope tags such as FLAG, processing sites such as phosphorylation, ubiquitination or protease recognition/cleavage sites, etc.

Exemplary bifunctional fusion proteins are shown in Table I.

| Ref No. | GFP Variant Moiety | Annexin Moiety, residues | Linker | GFP Activity | Annexin Activity |
|---|---|---|---|---|---|
| T65V-I | S65T | hV (SEQ ID NO:1, residues 1–320) | φ | +++ | +++ |
| T65V-II | S65T | hV (SEQ ID NO:1, residues 12–320) | Gly | +++ | +++ |
| T65V-III | S65T | hV (SEQ ID NO:1, residues 3–319) | Ala | +++ | +++ |
| T65V-IV | S65T | mV (SEQ ID NO:2, residues 1–319) | (Ala)$_3$ | +++ | +++ |
| T65V-V | S65T | rV (SEQ ID NO:3, residues 12–318) | (Ala)$_9$ | +++ | +++ |
| T65IV-I | S65T | hIV (SEQ ID NO:4, residues 1–321) | FLAG | +++ | +++ |
| T65III-I | S65T | hIII (SEQ ID NO:5, residues 1–323) | φ | +++ | ++ |
| H66V-I | Y66H | hV (SEQ ID NO:1, residues 12–320) | Gly | +++ | +++ |
| W66V-I | Y66W | hV (SEQ ID NO:1, residues 6–320) | (AlaGly)$_2$ | +++ | +++ |
| L64III-I | F64L | hIII (SEQ ID NO:1, residues 6–323) | Ala | +++ | ++ |
| H66I-I | S65T | hI (SEQ ID NO:6, residues 1–346) | GlyAlaGly | +++ | +++ |
| T65I-I | S65T | hI (SEQ ID NO:6, residues 41–346) | AlaSerAla | +++ | +++ |

The invention provides recombinant nucleic acids encoding the subject fusion proteins. Typically, natural isolated nucleic acids encoding the GFP and annexin moieties are spliced into expression constructs using conventional methodologies, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) and references cited herein. Alternatively, the amino acid sequences of the subject peptides are used to back-translate peptide-encoding nucleic acids optimized for selected expression systems (Holler et al. (1993) Gene 136, 323–328; Martin et al. (1995) Gene 154, 150–166). In either instance, the constructs are designed for expression in any conventional system, such as bacterial, insect, plant and mammalian expression systems. The proteins are preferably secreted and/or expressed in soluble form; preferably most of the protein secreted by or retained within the host cell is in soluble form. Preferred soluble expression avoids denaturation/renaturation and permits single step affinity purification of >90%, preferably >95%, preferably in a yield of at least 10, more preferably at least 25 mg/L. In a particular embodiment, the temperature of the expressing host is reduced at least 5, preferably at least 10, more preferably at least 15° C. below physiological or environmental temperature for the host (e.g. below 37° C. for *E. coli* or human cells).

Uses of the subject fusion proteins include selective cellular and biochemical labeling, particularly anionic species, such as anionic phospholipids. The subject proteins may be exposed to the targeted cellular or biochemical component in any convenient way, e.g. direct exogenous addition, indirectly by introduction into a cell and expression of a fusion protein encoding nucleic acid, etc., In a particular embodiment, the fusion proteins are used to selectively label apoptotic, dead and/or injured cells.

Without further description, one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure. Other generic configurations will be apparent to one skilled in the art. All publications and patent applications cited in this specification, and cited references therein, are herein incorporated by reference as if each individual publication, patent application or reference were specifically and individually indicated to be incorporated by reference.

EXAMPLES

Plasmid construction. Parental annexin plasmids for construction of GFP annexin fusions were constructed as previously described in published literature (e.g. Seaton, 1995, supra and citations therein). For example, the parent plasmid for construction of the GFP-annexin V fusion was pET9dE2, which were previously constructed and used for expression of human annexin V (Ernst, 1994, supra). Similarly, constructs encoding a panel of GFPs are constructed using commercially available and/or published material and methods (e.g. U.S. Pat. No. 5,491,084; Clontechniques, April 1997; Kaln, 1997, Biotechnol. International 8/97; Heim and Tsien, 1996, Current Biology 6, 178–182). For example, the open reading frame of green fluorescent protein (S65T variant) was amplified by PCR using pS65T-C1 (Clontech) as template and primers designed to incorporate sites for Rca I for ligation to the Nco I site of pET9dE2. In this case, the forward primer introduces a change in codon 2 to encode serine (as in wild-type GFP) rather than the glycine encoded by the template plasmid; and the backward primer eliminates the stop codon at the 3' end of the GFP open reading frame and introduces an alanine codon to form the junction with the 5' end of annexin V. After digestion of the PCR product with Rca I, it was ligated to Nco I-digested pET9dE2 and used to transform *E. coli* DH5α, and transformants that contained the GFP fragment in the correct orientation were used to transform *E. coli* BL-21(DE3) for protein expression.

Expression and purification of protein. Initial attempts at protein expression under standard conditions (growth at 37° C., induction with 0.4 mM IPTG) yielded brightly fluorescent but insoluble protein. Consequently, procedures were devised for expression of soluble, bifunctional proteins. In one embodiment, the GFP-annexin fusion proteins were expressed in *E. coli* BL-21(DE3) by growth in LB media at room temperature for 18–20 hours, without IPTG induction. This resulted in fusion proteins that were bright green and present in the soluble fraction (approximately 80%) after lysozyme digestion and probe sonication of the bacterial suspension. After adding calcium (2.5 mM) to the supernatant fraction of the *E. coli* lysate, GFP-annexins were purified by affinity chromatography using phospholipids (e.g. phosphatidylserine) immobilized on controlled-pore glass (Ernst, J. D., et al. (1991) J. Biol. Chem. 266, 6670–6673; Ernst, J. D. (1991) J. Immunol. 146, 3110–3114; Ernst, 1994).

Characterization of GFP-annexin. Fluorescence excitation and emission spectra were obtained using an SLM8000C spectrofluorimeter equipped with motorized excitation and emission monochromators and bandpass settings of 4 nm. Phospholipid-containing liposomes were prepared as previously described (Ernst, 1994, supra).

Studies of apoptotic cells. Rabbit and human pleural mesothelial cells were plated in 6 well plates at near confluency. For the experiments detailed below, cells were incubated overnight in the apoptotic stimuli, crocidolite (5–20 $\mu$g/cm$^2$) or actinomycin D (0.33 $\mu$M), in serum-free conditions to avoid serum coating onto the asbestos fiber. After floating cells were collected by aspiration of medium, attached cells were detached with trypsin (2.5%) and added to the floating cells. Cells were kept on ice to minimize ongoing apoptosis. Cells exposed to asbestos fibers were filtered through a 100 $\mu$m cell strainer to remove fibers prior to flow cytometric analysis. Cells (approximately 2–5×10$^5$ cells per condition) were then spun and resuspended in 200 $\mu$l of annexin buffer (Hank's buffer with 15 mM Hepes and 2 mM total calcium concentration [1.3 mM in the Hank's plus an additional 0.7 mM CaCl$_2$]).

Cells (2–5×10$^5$ in 200 $\mu$l) were incubated with GFP-annexin or FITC-annexin (both at 3 $\mu$g/ml) for 10 min on ice. Immediately prior to analysis by flow cytometry, propidium iodide (15 $\mu$g/ml, Sigma Chemical Co.) was added to each tube. No further washing and no fixation was performed.

Cells on ice were analysed by flow cytometry (FACSort, Becton Dickinson, San Jose, Calif.) with acquisition and data analysis using CELLQuest Software (Becton Dickinson). Compensation for the use of two fluorescent probes was set using control cells stained with either GFP-annexin or propidium iodide alone. 10,000 events per sample were acquired to ensure adequate mean data.

For detection of intracellular antigens, cells require fixation and permeabilization. To determine if GFP-annexin binding would be altered by those conditions, various fixatives and permeabilization were tested. During these studies, the calcium concentration was increased to 5 mM. After cells were stained with GFP-annexin as above, cells were washed twice in annexin buffer to remove all free GFP-annexin. To determine the stability of the bound GFP-annexin during fixation, the cells were then fixed with either glutaraldehyde (0.5–2%) or paraformaldehyde (2–4%) for 10 min in the dark. The cells were then washed in annexin buffer (with 5 mM CaCl$_2$) and perrneabilized with Triton 0.1% in the same buffer for 4 min. Following an additional wash, cells were resuspended in annexin buffer (with 5 mM CaCl$_2$) for analysis of GFP-annexin binding.

Expression and purification of GFP-annexins: Under the low temperature expression conditions, approximately 80% of the GFP-annexins expressed were present in the soluble fraction of the *E. coli* lysate, and generally >90% could be isolated to purity in single step phospholipid affinity chromatography. For example, GFP-annexin V proteins were isolated to >90% purity in a single step by calcium-dependent phosphatidylserine affinity chromatography. This served as an efficient purification step as well as providing evidence that the phospholipid binding ability of the annexin domains were preserved in these chimera. Another chimeric protein in which GFP was fused to the carboxyl terminus of annexin V was also soluble and fluorescent, but did not bind phosphatidylserine. The isolated proteins had the electrophoretic mobility predicted by amino acid compositions (61 kDa for annexin V fusions), were recognized by an antibody to the annexin moiety, and exhibited SDS-resistant fluorescence with UV transillumination of the gel and exhibited the functional properties of both antecedents. The failure of an annexin V fusion protein that contained the moieties in the contrasting orientation (e.g., GFP fused to the carboxyl terminus of annexin V) to bind phospholipids was unexpected and may have been the result of the GFP domain masking the phospholipid binding surface of the annexin.

Fluorescence properties of GFP-annexins. To assure that the fuision of annexins to GFPs did not reduce the fluorescence properties of the GFP moieies, the excitation and emission spectra of the GFP-annexin fusion proteins were examined and the spectra of the GFPs found undimin;shed. For example, the GFP(S65T)-annexin V fuision proteins exhibited a discrete peak of fluorescence emission centered at 512 nm when excited at 490 nm. Consistent with the prior observation that the alteration of residue 65 from serine to threonine causes loss of excitation of GFP in the near ultraviolet range, there was no fluorescence detected when these GFP-annexin V chimeras were excited at 375 nm. When fluorescence emission was monitored at 510 nm, there was a single major excitation peak at 465–495 nm, with a minor trough at 480 nm. The fluorescence spectra were unaffected by the addition of calcium (1.0 mM), phosphatidylserine-containing liposomes (1.0 $\mu$M), or both. These GFP-containing proteins are ideally suited for use with the argon-laser based flow cytometers (excitation at 488 nm/detection at 530 nm).

Use of GFP-annexin V to detect apoptotic cells by flow cytometry. To determine whether the annexin V chimeras retained the ability of annexin V to bind apoptotic cells in a specific and calcium-dependent manner, a well-characterized model system of apoptosis of pleural mesothelial cells was used (Broaddus, 1996, supra). GFP-annexin V chimeras did not bind to normal cells, but exhibited saturable binding to apoptotic mesothelial cells as detected by flow cytometry. Compared to FITC-annexin V, fluorescence of GFP-annexin V chimera-labeled apoptotic cells was 5 times brighter, despite using GFP-annexin V chimeras at approximately ½ the molar concentration of FITC-annexin V. In these experiments, staining with either FITC-annexin V or GFP-annexin V chimeras provided a more sensitive detection of apoptotic cells than staining with acridine orange. Binding of GFP-annexin V chimeras to apoptotic cells was calcium-dependent, and could be competitively antagonized by unlabeled annexin V. Therefore, in addition to retaining the fluorescence properties of GFP, GFP-annexin V chimeras also retain the ability of annexin V to specifically detect exposure of anionic phospholipids on the outer leaflet of the plasma membrane of apoptotic cells. GFP-annexin V chimeras could also be used in experiments in which exclusion of propidium iodide (PI) was used to distinguish early apoptotic (GFP-annexin V+, PI–) cells from late apoptotic or necrotic cells (GFP-annexin V+, PI+).

In studies of apoptosis in vivo, it may be important to identify the cell type undergoing apoptosis. One means of phenotyping apoptosis cells is to costain with an antibody that identifies a specific cell type. Some cells, for example mesothelial cells have no unique cell surface antigen and must be identified by intracellular expression of intermediate filaments, namely cytokeratin. Access of antibodies to this or other intracellular antigens requires cell permeabilization with detergent, which disrupts the integrity of plasma membrane phospholipids. When apoptotic cells were first labeled with GFP-annexin V chimeras, washed to remove unbound fusion protein, fixed with paraformaldehyde or glutaraldehyde, and permeabilized with 0.1% Triton X-100, GFP-annexin V chimera binding was retained. Moreover, after staining with a monoclonal antibody to cytokeratin and PE-labeled goat anti-mouse IgG, two-color flow cytometry could be used to identify and enumerate apoptotic mesothelial cells in a mixture of cells (lymphocytes, macrophages, and neutrophils) obtained from the pleural space of rabbits treated with crocidolite asbestos.

Due to their bifunctional properties, GFP-annexins are useful reagents for further studies of apoptosis and of disorders of the erythrocyte membrane that are characterized by loss of phospholipid asymmetry and exposure of anionic phospholipids (Kuypers, F. A., et al. (1996) Blood 87, 1179–1187; Wood, B. L., Gibson, D. F. and Tait, J. F. (1996) Blood 88, 1873–80). In addition to the utility of GFP-annexins as reagents for studying membrane phospholipids, the approach described here is useful in constructing annexin fusions to GFP to study the interaction of specific annexins with intracellular membranes in intact cells. Annexins have been found to interact with membranes of phagosomes, endosomes, and intracellular vesicles containing microbial pathogens (Ernst, 1991, supra; Emans, N., et al. (1993) J Cell Biol 120, 1357–1369; Desjardins, M., et al. (1994) J Biol Chem 269, 32194–200; Majeed, M., et al. (1994) Infect Immun 62, 127–134; Diakonova, M., et al. (1997) J Cell Sci 110, 1199–213). The ability to use bifunctional GFP-annexin fusion proteins that are functionally well-characterized to study the interaction of annexins with intracellular membranes will further advance the understanding of the intracellular functions of the annexin proteins.

What is claimed is:

1. A bacterium comprising a soluble recombinant polypeptide comprising a bifunctional green fluorescent protein (GFP)—annexin fusion protein, wherein said GFP is an *Aequorea Victoria* GFP or a variant thereof, said fusion protein comprising GFP and annexin moieties which provide undiminished fluorescent intensity and anionic phospholipid binding affinity as compared with the corresponding unfused GFP and annexin.

2. The bacterium of claim 1, wherein the GFP and annexin moieties are selected from: S65T GFP variant/hAnnexinV, residues 1–320 (SEQ ID NO:1, residues 1–320); S65T GFP variant/hAnnexinV, residues 12–320 (SEQ ID NO:1, residues 12–320); S65T GFP variant/hAnnexinV, residues 3–319 (SEQ ID NO:1, residues 3–319); S65T GFP variant/mAnnexinV, residues 1–319 (SEQ ID NO:2, residues 1–319); S65T GFP variant/rAnnexinV, residues 12–318 (SEQ ID NO:3, residues 12–318); S65T GFP variant/hAnnexinIV, residues 1–321 (SEQ ID NO:4, residues 1–321); S65T GFP variant/hAnnexinIII, residues 1–323 (SEQ ID NO:5, residues 1–323); Y66H GFP variant/hAnnexinV, residues 12–320 (SEQ ID NO:1, residues 12–320); Y66W GFP variant/hAnnexinV, residues 6–320 (SEQ ID NO:1, residues 6–320); F64L GFP variant/hAnnexinIII, residues 6–323 (SEQ ID NO:5, residues 6–323); S65T GFP variant/hAnnexinI, residues 1–346 (SEQ ID NO:6, residues 1–346); and S65T GFP variant/hAnnexinI, residues 41–346 (SEQ ID NO:6, residues 41–346).

3. The bacterium of claim 1, wherein the bacterium is *E. coli*.

4. The bacterium of claim 1, wherein the bacterium is *E. coli* and the polypeptide is expressed in said bacterium at a temperature of 32° C. or less.

5. The bacterium of claim 1, wherein the bacterium is *E. coli* and the polypeptide is expressed in said bacterium at a temperature of 27° C. or less.

6. The bacterium of claim 1, wherein the bacterium is *E. coli* and the polypeptide is expressed in said bacterium at a temperature of between 32 and 22° C.

7. The bacterium of claim 1, wherein the GFP and annexin moieties are separated by a linker peptide.

8. The bacterium of claim 1, wherein the GFP and annexin moieties are separated by a linker peptide comprising at least one of an alanine, polyalanine, glycine, polyglycine, epitope tag, processing site and protease recognition or cleavage site.

9. The bacterium of claim 1, wherein the annexin moiety is human, mouse or rat.

10. The bacterium of claim 1, wherein the phospholipid is phoshotidylserine.

11. A method of making a polypeptide comprising a bifunctional green fluorescent protein (GFP)—annexin fusion protein, wherein said GFP is an *Aequorea victoria* GFP or a variant thereof, said method comprising the step of culturing a bacterium comprising a nucleic acid encoding the polypeptide under conditions wherein the polypeptide is solubly expressed within the bacterium, said fusion protein comprising GFP and annexin moieties which provide undiminished fluorescent intensity and anionic phospholipid binding affinity as compared with the corresponding unfused GFP and annexin.

12. The method of claim 11, wherein the GFP and annexin moieties are selected from: S65T GFP variant/hAnnexinV, residues 1–320 (SEQ ID NO:1, residues 1–320); S65T GFP variant/hAnnexinV, residues 12–320 (SEQ ID NO:1, residues 12–320); S65T GFP variant/hAnnexinV, residues 3–319 (SEQ ID NO:1, residues 3–319); S65T GFP variant/mAnnexinV, residues 1–319 (SEQ ID NO:2, residues 1–319); S65T GFP variant/rAnnexinV, residues 12–318 (SEQ ID NO:3, residues 12–318); S65T GFP variant/hAnnexinIV, residues 1–321 (SEQ ID NO:4, residues 1–321); S65T GFP variant/hAnnexinIII, residues 1–323 (SEQ ID NO:5, residues 1–323); Y66H GFP variant/hAnnexinV, residues 12–320 (SEQ ID NO:1, residues 12–320); Y66W GFP variant/hAnnexinV, residues 6–320 (SEQ ID NO:1, residues 6–320); F64L GFP variant/hAnnexinIII, residues 6–323 (SEQ ID NO:5, residues 6–323); S65T GFP variant/hAnnexinI, residues 1–346 (SEQ ID NO:6, residues 1–346); and S65T GFP variant/hAnnexinI, residues 41–346 (SEQ ID NO:6, residues 41–346).

13. The method of claim 11, wherein the bacterium is *E. coli*.

14. The method of claim 11, wherein the bacterium is *E. coli* and the polypeptide is expressed in said bacterium at a temperature of 32° C. or less.

15. The method of claim 11, wherein the bacterium is *E. coli* and the polypeptide is expressed in said bacterium at a temperature of 27° C. or less.

16. The method of claim 11, wherein the bacterium is *E. coli* and the polypeptide is expressed in said bacterium at a temperature of between 32 and 22° C.

17. The method of claim 11, wherein the GFP and annexin moieties are separated by a linker peptide.

18. The method of claim 11, wherein the GFP and annexin moieties are separated by a linker peptide comprising at least one of an alanine, polyalanine, glycine, polyglycine, epitope tag, processing site and protease recognition or cleavage site.

19. The method of claim 11, wherein the annexin moiety is human, mouse or rat.

20. The method of claim 11, wherein the phospholipid is phosphotidylserine.

21. A method of making a polypeptide comprising a bifunctional GFP-annexin fusion protein, said method comprising the steps of culturing a bacterium comprising a nucleic acid encoding a polypeptide according to claim 1 under conditions wherein the polypeptide is solubly expressed within the bacterium, and purifying the polypeptide from the bacterium, wherein the bacterium is *E. coli*, the culturing step comprises expression of the polypeptide at a temperature below 37° C. and the purifying step comprises affinity chromatograhy.

* * * * *

SEQUENCE LISTING

```
<160> NUMBER OF SEQ ID NOS: 6

<210> SEQ ID NO 1
<211> LENGTH: 320
<212> TYPE: PRT
<213> ORGANISM: human

<400> SEQUENCE: 1

Met Ala Gln Val Leu Arg Gly Thr Val Thr Asp Phe Pro Gly Phe Asp
  1               5                  10                  15

Glu Arg Ala Asp Ala Glu Thr Leu Arg Lys Ala Met Lys Gly Leu Gly
                 20                  25                  30

Thr Asp Glu Glu Ser Ile Leu Thr Leu Leu Thr Ser Arg Ser Asn Ala
             35                  40                  45

Gln Arg Gln Glu Ile Ser Ala Ala Phe Lys Thr Leu Phe Gly Arg Asp
         50                  55                  60

Leu Leu Asp Asp Leu Lys Ser Glu Leu Thr Gly Lys Phe Glu Lys Leu
 65                  70                  75                  80

Ile Val Ala Leu Met Lys Pro Ser Arg Leu Tyr Asp Ala Tyr Glu Leu
                 85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220
```

Ile Asp Arg Glu Thr Ser Gly Asn Leu Glu Gln Leu Leu Ala Val
225                 230                 235                 240

Val Lys Ser Ile Arg Ser Ile Pro Ala Tyr Leu Ala Glu Thr Leu Tyr
            245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
            275                 280                 285

Arg Lys Asn Phe Ala Thr Ser Leu Tyr Ser Met Ile Lys Gly Asp Thr
            290                 295                 300

Ser Gly Asp Tyr Lys Lys Ala Leu Leu Leu Cys Gly Glu Asp Asp
305                 310                 315                 320

<210> SEQ ID NO 2
<211> LENGTH: 319
<212> TYPE: PRT
<213> ORGANISM: mouse

<400> SEQUENCE: 2

Met Ala Thr Arg Gly Thr Val Thr Asp Phe Pro Gly Phe Asp Gly Arg
1               5                   10                  15

Ala Asp Ala Glu Val Leu Arg Lys Ala Met Lys Gly Leu Gly Thr Asp
            20                  25                  30

Glu Asp Ser Ile Leu Asn Leu Leu Thr Ser Arg Ser Asn Ala Gln Arg
        35                  40                  45

Gln Glu Ile Ala Gln Glu Phe Lys Thr Leu Phe Gly Arg Asp Leu Val
    50                  55                  60

Asp Asp Leu Lys Ser Glu Leu Thr Gly Lys Phe Glu Lys Leu Ile Val
65                  70                  75                  80

Ala Met Met Lys Pro Ser Arg Leu Tyr Asp Ala Tyr Glu Leu Lys His
                85                  90                  95

Ala Leu Lys Gly Ala Gly Thr Asp Glu Lys Val Leu Thr Glu Ile Ile
            100                 105                 110

Ala Ser Arg Thr Pro Glu Glu Leu Ser Ala Ile Lys Gln Val Tyr Glu
        115                 120                 125

Glu Glu Tyr Gly Ser Asn Leu Glu Asp Asp Val Gly Asp Thr Ser
    130                 135                 140

Gly Tyr Tyr Gln Arg Met Leu Val Val Leu Leu Gln Ala Asn Arg Asp
145                 150                 155                 160

Pro Asp Thr Ala Ile Asp Asp Ala Gln Val Glu Leu Asp Ala Gln Ala
                165                 170                 175

Leu Phe Gln Ala Gly Glu Leu Lys Trp Gly Thr Asp Glu Glu Lys Phe
            180                 185                 190

Ile Thr Ile Phe Gly Thr Arg Ser Val Ser His Leu Arg Arg Val Phe
        195                 200                 205

Asp Lys Tyr Met Thr Ile Ser Gly Phe Gln Ile Glu Glu Thr Ile Asp
    210                 215                 220

Arg Glu Thr Ser Gly Asn Leu Glu Gln Leu Leu Leu Ala Val Val Lys
225                 230                 235                 240

Ser Ile Arg Ser Ile Pro Ala Tyr Leu Ala Glu Thr Leu Tyr Tyr Ala
                245                 250                 255

Met Lys Gly Ala Gly Thr Asp Asp His Thr Leu Ile Arg Val Val Val
            260                 265                 270

```
Ser Arg Ser Glu Ile Asp Leu Phe Asn Ile Arg Lys Glu Phe Arg Lys
        275                 280                 285

Asn Phe Ala Thr Ser Leu Tyr Ser Met Ile Lys Gly Asp Thr Ser Gly
        290                 295                 300

Asp Tyr Lys Lys Ala Leu Leu Leu Cys Gly Gly Glu Asp Asp
305                 310                 315

<210> SEQ ID NO 3
<211> LENGTH: 318
<212> TYPE: PRT
<213> ORGANISM: rat

<400> SEQUENCE: 3

Ala Leu Arg Gly Thr Val Thr Asp Phe Ser Gly Phe Asp Gly Arg Ala
1               5                   10                  15

Asp Ala Glu Val Leu Arg Lys Ala Met Lys Gly Leu Gly Thr Asp Glu
            20                  25                  30

Asp Ser Ile Leu Asn Leu Leu Thr Ala Arg Ser Asn Ala Gln Arg Gln
        35                  40                  45

Gln Ile Ala Glu Glu Phe Lys Thr Leu Phe Gly Arg Asp Leu Val Asn
    50                  55                  60

Asp Met Lys Ser Glu Leu Thr Gly Lys Phe Glu Lys Leu Ile Val Ala
65                  70                  75                  80

Leu Met Lys Pro Ser Arg Leu Tyr Asp Ala Tyr Glu Leu Lys His Ala
                85                  90                  95

Leu Lys Gly Ala Gly Thr Asp Glu Lys Val Leu Thr Glu Ile Ile Ala
            100                 105                 110

Ser Arg Thr Pro Glu Glu Leu Arg Ala Ile Lys Gln Ala Tyr Glu Glu
        115                 120                 125

Glu Tyr Gly Ser Asn Leu Glu Asp Asp Val Val Gly Asp Thr Ser Gly
    130                 135                 140

Tyr Tyr Gln Arg Met Leu Val Val Leu Leu Gln Ala Asn Arg Asp Pro
145                 150                 155                 160

Asp Thr Ala Ile Asp Asp Ala Gln Val Glu Leu Asp Ala Gln Ala Leu
                165                 170                 175

Phe Gln Ala Gly Glu Leu Lys Trp Gly Thr Asp Glu Glu Lys Phe Ile
            180                 185                 190

Thr Ile Leu Gly Thr Arg Ser Val Ser His Leu Arg Arg Val Phe Asp
        195                 200                 205

Lys Tyr Met Thr Ile Ser Gly Phe Gln Ile Glu Glu Thr Ile Asp Arg
    210                 215                 220

Glu Thr Ser Gly Asn Leu Glu Asn Leu Leu Leu Ala Val Val Lys Ser
225                 230                 235                 240

Ile Arg Ser Ile Pro Ala Tyr Leu Ala Glu Thr Leu Tyr Tyr Ala Met
                245                 250                 255

Lys Gly Ala Gly Thr Asp Asp His Thr Leu Ile Arg Val Ile Val Ser
            260                 265                 270

Arg Ser Glu Ile Asp Leu Phe Asn Ile Arg Lys Glu Phe Arg Lys Asn
        275                 280                 285

Phe Ala Thr Ser Leu Tyr Ser Met Ile Lys Gly Asp Thr Ser Gly Asp
    290                 295                 300

Tyr Lys Lys Ala Leu Leu Leu Cys Gly Gly Glu Asp Asp
305                 310                 315
```

```
<210> SEQ ID NO 4
<211> LENGTH: 321
<212> TYPE: PRT
<213> ORGANISM: human

<400> SEQUENCE: 4

Met Ala Met Ala Thr Lys Gly Thr Val Lys Ala Ala Ser Gly Phe
 1               5                  10                  15

Asn Ala Met Glu Asp Ala Gln Thr Leu Arg Lys Ala Met Lys Gly Leu
                20                  25                  30

Gly Thr Asp Glu Asp Ala Ile Ile Ser Val Leu Ala Tyr Arg Asn Thr
            35                  40                  45

Ala Gln Arg Gln Glu Ile Arg Thr Ala Tyr Lys Ser Thr Ile Gly Arg
        50                  55                  60

Asp Leu Ile Asp Asp Leu Lys Ser Glu Leu Ser Gly Asn Phe Glu Gln
 65                  70                  75                  80

Val Ile Val Gly Met Met Thr Pro Thr Val Leu Tyr Asp Val Gln Glu
                85                  90                  95

Leu Arg Arg Ala Met Lys Gly Ala Gly Thr Asp Glu Gly Cys Leu Ile
                100                 105                 110

Glu Ile Leu Ala Ser Arg Thr Pro Glu Glu Ile Arg Arg Ile Ser Gln
            115                 120                 125

Thr Tyr Gln Gln Gln Tyr Gly Arg Ser Leu Glu Asp Asp Ile Arg Ser
        130                 135                 140

Asp Thr Ser Phe Met Phe Gln Arg Val Leu Val Ser Leu Ser Ala Gly
145                 150                 155                 160

Gly Arg Asp Glu Gly Asn Tyr Leu Asp Asp Ala Leu Val Arg Gln Asp
                165                 170                 175

Ala Gln Asp Leu Tyr Glu Ala Gly Glu Lys Lys Trp Gly Thr Asp Glu
            180                 185                 190

Val Lys Phe Leu Thr Val Leu Cys Ser Arg Asn Arg Asn His Leu Leu
        195                 200                 205

His Val Phe Asp Glu Tyr Lys Arg Ile Ser Gln Lys Asp Ile Glu Gln
    210                 215                 220

Ser Ile Lys Ser Glu Thr Ser Gly Ser Phe Glu Asp Ala Leu Leu Ala
225                 230                 235                 240

Ile Val Lys Cys Met Arg Asn Lys Ser Ala Tyr Phe Ala Glu Lys Leu
                245                 250                 255

Tyr Lys Ser Met Lys Gly Leu Gly Thr Asp Asp Asn Thr Leu Ile Arg
            260                 265                 270

Val Met Val Ser Arg Ala Glu Ile Asp Met Leu Asp Ile Arg Ala His
        275                 280                 285

Phe Lys Arg Leu Tyr Gly Lys Ser Leu Tyr Ser Phe Ile Lys Gly Asp
    290                 295                 300

Thr Ser Gly Asp Tyr Arg Lys Val Leu Leu Val Leu Cys Gly Gly Asp
305                 310                 315                 320

Asp

<210> SEQ ID NO 5
<211> LENGTH: 323
<212> TYPE: PRT
<213> ORGANISM: human

<400> SEQUENCE: 5

Ser Ala Ser Ile Trp Val Gly His Arg Gly Thr Val Arg Asp Tyr Pro
 1               5                  10                  15
```

```
Asp Phe Ser Pro Ser Val Asp Ala Glu Ala Ile Gln Lys Ala Ile Arg
                20                  25                  30
Gly Ile Gly Thr Asp Glu Lys Met Leu Ile Ser Ile Leu Thr Glu Arg
            35                  40                  45
Ser Asn Ala Gln Arg Gln Leu Ile Val Lys Glu Tyr Gln Ala Ala Tyr
        50                  55                  60
Gly Lys Glu Leu Lys Asp Asp Leu Lys Gly Asp Leu Ser Gly His Phe
65                  70                  75                  80
Glu His Leu Met Val Ala Leu Val Thr Pro Pro Ala Val Phe Asp Ala
                85                  90                  95
Lys Gln Leu Lys Lys Ser Met Lys Gly Ala Gly Thr Asn Glu Asp Ala
                100                 105                 110
Leu Ile Glu Ile Leu Thr Thr Arg Thr Ser Arg Gln Met Lys Asp Ile
            115                 120                 125
Ser Gln Ala Tyr Tyr Thr Val Tyr Lys Lys Ser Leu Gly Asp Asp Ile
        130                 135                 140
Ser Ser Glu Thr Ser Gly Asp Phe Arg Lys Ala Leu Leu Thr Leu Ala
145                 150                 155                 160
Asp Gly Arg Arg Asp Glu Ser Leu Lys Val Asp Glu His Leu Ala Lys
                165                 170                 175
Gln Asp Ala Gln Ile Leu Tyr Lys Ala Gly Glu Asn Arg Trp Gly Thr
                180                 185                 190
Asp Glu Asp Lys Phe Thr Glu Ile Leu Cys Leu Arg Ser Phe Pro Gln
            195                 200                 205
Leu Lys Leu Thr Phe Asp Glu Tyr Arg Asn Ile Ser Gln Lys Asp Ile
        210                 215                 220
Val Asp Ser Ile Lys Gly Glu Leu Ser Gly His Phe Glu Asp Leu Leu
225                 230                 235                 240
Leu Ala Ile Val Asn Cys Val Arg Asn Thr Pro Ala Phe Leu Ala Glu
                245                 250                 255
Arg Leu His Arg Ala Leu Lys Gly Ile Gly Thr Asp Glu Phe Thr Leu
                260                 265                 270
Asn Arg Ile Met Val Ser Arg Ser Glu Ile Asp Leu Leu Asp Ile Arg
            275                 280                 285
Thr Glu Phe Lys Lys His Tyr Gly Tyr Ser Leu Tyr Ser Ala Ile Lys
        290                 295                 300
Ser Asp Thr Ser Gly Asp Tyr Glu Ile Thr Leu Leu Lys Ile Cys Gly
305                 310                 315                 320
Gly Asp Asp

<210> SEQ ID NO 6
<211> LENGTH: 346
<212> TYPE: PRT
<213> ORGANISM: human

<400> SEQUENCE: 6

Met Ala Met Val Ser Glu Phe Leu Lys Gln Ala Trp Phe Ile Glu Asn
1               5                   10                  15
Glu Glu Gln Glu Tyr Val Gln Thr Val Lys Ser Ser Lys Gly Gly Pro
                20                  25                  30
Gly Ser Ala Val Ser Pro Tyr Pro Thr Phe Asn Pro Ser Ser Asp Val
            35                  40                  45
Ala Ala Leu His Lys Ala Ile Met Val Lys Gly Val Asp Glu Ala Thr
        50                  55                  60
```

-continued

```
Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
                100                 105                 110

Lys Thr Pro Ala Gln Phe Asp Ala Asp Glu Leu Arg Ala Ala Met Lys
            115                 120                 125

Gly Leu Gly Thr Asp Glu Asp Thr Leu Ile Glu Ile Leu Ala Ser Arg
            130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
                180                 185                 190

Gly Val Asn Glu Asp Leu Ala Asp Ser Asp Ala Arg Ala Leu Tyr Glu
            195                 200                 205

Ala Gly Glu Arg Arg Lys Gly Thr Asp Val Asn Val Phe Asn Thr Ile
210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
        290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345
```